United States Patent [19]

Dahms

[11] 3,964,864

[45] June 22, 1976

[54] METHOD AND APPARATUS FOR MEASUREING $CO_2$, $O_2$, AND Cl IN BODY FLUIDS

[76] Inventor: Harald Dahms, 22 Lakeview Road, Ossining, N.Y. 10562

[22] Filed: Nov. 18, 1974

[21] Appl. No.: 524,793

[52] U.S. Cl. ............................ 23/230 B; 23/232 E; 23/253 R; 73/19
[51] Int. Cl.² ................... G01N 33/16; G01N 27/18
[58] Field of Search.......... 23/230 B, 232 R, 232 E, 23/253 R, 254 R; 73/19, 23, 25; 128/2 G

[56] References Cited
UNITED STATES PATENTS

| | | | |
|---|---|---|---|
| 2,680,060 | 6/1954 | Natelson | 23/230 B X |
| 3,097,518 | 7/1963 | Taylor et al. | 23/253 R |
| 3,118,736 | 1/1964 | Taylor | 23/230 B |
| 3,150,516 | 9/1964 | Linnenbom et al. | 73/19 |
| 3,756,782 | 9/1973 | Phillips | 23/230 B |

*Primary Examiner*—Joseph Scovronek
*Assistant Examiner*—Timothy W. Hagan

[57] ABSTRACT

A method and apparatus for measuring $CO_2$, $O_2$ and chlorides in body fluids, such as whole blood, blood serum and plasma, etc. A reagent and a known amount of sample to be tested react in a closed vessel to release the gas to be measured into a gas space. A displacement liquid is then introduced to expel the released gas in the gas space to a detector, where its concentration in a stationary gas sample is measured. The mixture of sample, reagent, and gas is then drained from the vessel and from the detector and a reverse flow of excess flushing fluid (gas) is moved through the detector and vessel to flush the apparatus so that another measurement can begin.

47 Claims, 2 Drawing Figures

FIG. 2

METHOD AND APPARATUS FOR MEASURING $CO_2$, $O_2$, AND CL IN BODY FLUIDS

BACKGROUND OF THE INVENTION

1. Field of the Invention

This invention relates to the determination of $CO_2$, $O_2$ and Cl in body fluids such as blood, and more particularly to an improved method and apparatus for performing such measurements reliably, cheaply, and quickly.

2. Description of the Prior Art

The determination of blood gases is important for clinical analysis. In particular, the determination of carbon dioxide ($CO_2$) and oxygen ($O_2$) content in whole blood and blood serum are among the most frequently performed analyses in a clinical laboratory. Due to the great importance of these analyses, a number of techniques have been developed and are presently being used to determine $CO_2$ and $O_2$ concentration.

The traditional technique used for the determination of $CO_2$ in blood is the method of D. D. Van Slyke which was published in the Journal of Biological Chemistry, Vol. 61, page 523 (1924). In the basic Van Slyke method, blood serum and acid are mixed in a closed volume and the carbon dioxide in the blood is extracted from the blood by application of vacuum. The extracted carbon dioxide is then measured volumetrically or manometrically. When the vacuum is drawn, other blood gases are released from the serum in addition to the carbon dioxide. This requires that a base, such as sodium hydroxide, be added in order to separate the carbon dioxide from the other released gases. After this, the volumetric measurement is performed by known techniques.

The Van Slyke method is practiced in numerous devices, as for instance in the microgasometers described by S. Natelson in U.S. Pat. Nos. 2,680,060 and 3,171,722. These microgasometers are described in more detail in publication P-5/64, distributed by Scientific Industries, Inc., 220-05 97th Avenue, Queens Village 29, New York, N.Y.

Natelson describes various techniques for connecting his apparatus to a gas chromatograph so that gases liberated from the blood serum may be analyzed in the gas chromatograph. Of course, considerable numbers of papers have been presented which describe the analysis of blood serum for carbon dioxide and other gases using gas chromatography. One of these articles is L. E. Farhi et al. "Determination of Dissolved $N_2$ in Blood by Gas Chromatography and (a-A) $N_2$ Difference", Journal of Applied Physiology, Vol. 18, No. 1, pages 97–106, January 1963. Another article of interest is T. Johns and B. Thompson "Gas Chromatographic Determination of Blood Gases", The Analyzer, Vol. 4, No. 2, April, 1963.

In gas chromatography, the released gases are typically carried in a gas stream over a chromatographic column and then through a detector. The gas stream used as the carrier is usually He, or some other gas having a different thermal conductivity than the gases which are to be measured. The column has different retention rates for different gases in the gas stream and acts to separate the different gases from one another. The detector is a flow detector which provides different peak responses for different gases to be measured. The detector is usually comprised of a hot filament wire whose resistance changes in accordance with the thermal conductivity of the gas which is in contact with the wire. Since the thermal conductivities of the gases to be measured are different from one another, and since the gases have been separated in a known order, each of the transient peaks of the detector response can be associated with one of the gases to be measured. These transient responses are usually plotted on a recorder, since the measurement is a dynamic one done in accordance with the flow of gases, rather than a stationary gas measurement. The integral under the response curve or the peak height of the response curve is then a measure of the gas concentration in the blood sample.

While there have been numerous publications on gas chromatography for determination of, for instance, $CO_2$ in blood serum, this technique has not found wide application in routine laboratory measurements. The technique is complex, requiring a significant amount of apparatus including the chromatograph and column, together with recording equipment. Additionally, the method is very time consuming. Part of the time consumption is due to the burdens placed on the operator of the apparatus, who has to inject the blood sample, and then wait until the sample passes through the column and the detector. The operator then has to relate the recorder output to the signal from a calibration sample, all of which is time consuming and which can lead to human error.

In addition to the disadvantages noted above, gas chromatography requires the use of a carrier gas stream. This is a dynamic measurement rather than a static measurement, and is consequently more complex and thus less reliable. With such a dynamic process, constant flow rates are required and transient responses have to be quickly recorded in order to provide accurate results.

In addition to those disadvantages, the carrier gas generally has to be a gas having a different thermal conductivity than the gas species to be detected, in order that the measurement of the detected gas species is not altered by the presence of the carrier gas. It is for this reason that gases such as He, which has a significantly different thermal conductivity than air, $O_2$, $N_2$, etc are used.

Another disadvantage of most prior art techniques for measuring blood gases concerns the use of a vacuum when the reagent and blood react to release the gases to be detected. Use of a vacuum means that species other than the gas to be measured (such as $CO_2$) will be released. For instance, $O_2$, $N_2$, etc. will be released from the blood and will contaminate the sample measurement where it is desired to measure $CO_2$.

Still another disadvantage of the use of vacuum relates to the possibility of leakage and lack of vacuum tightness. In vacuum systems, errors generally occur because apparatus such as valves and stopcocks develop leaks. Since the vacuum apparatus is designed to operate reliably only when reproducibly good vacuum is provided, such techniques are critically dependent on the reliability of components which are themselves subject to numerous problems. Consequently, it is important to provide a technique which suffers only minimal interference from dissolved gases in the blood other than the species which is to be measured.

Reference is also made to an instrument for measurement of $CO_2$, which was evaluated and reported on in Clinical Chemistry, Vol. 19, No. 10, 1227 (1973). This instrument is the "Harleco $CO_2$ Apparatus", sold by Harleco Co., Philadelphia, Pa. 19143. In this instrument, the gas is released into air and is measured by a volume displacement. The released gas is not pushed to a detector by a reagent, as in the present invention, and the instrument itself is very difficult to clean after each measurement. Also, at least 1.0 ml of serum or plasma is required, and therefore the instrument is not usable for most pediatric samples. Due to friction, the weight of the piston etc., the instrument has to be calibrated frequently.

In general, the prior art methods for measuring blood gases contain certain "non-equilibrium" features which lead to errors. For instance, the application of vacuum extracts gas from the blood which is partly reabsorbed by the blood when the vacuum is removed.

Also, the gas chromatographic methods involve the flow of gas through the system containing blood serum and gas. This causes a change in equilibrium of the system as the sample gas is swept away. That is, no time is available for the flowing gas to establish equilibrium between the flowing gas and the blood sample or at best only a partial equilibrium is obtained, so that it is difficult to establish a basis for the system in order to make a proper measurement.

In contrast with the prior art, the present invention uses an equilibrated, stationary system to obtain more accurate results, where very small samples can be evaluated. The apparatus is automatically cleaned after each measurement, thus insuring good accuracy and rapid measurement. Further, the blood gas measured by the detector has essentially the same composition as that originally established in the vessel, thereby insuring increased accuracy.

Accordingly, it is a primary object of this invention to provide a technique for low cost, reliable measurement of $CO_2$ and $O_2$ in body fluid samples such as whole blood and blood serum.

It is another object of this invention to provide an apparatus for measuring the $CO_2$ and $O_2$ content of body fluids under stationary equilibrium conditions.

It is still another object of this invention to provide an apparatus for the measurement of $CO_2$ and $O_2$ in body fluids which apparatus can be easily flushed after each measurement to provide increased reliability.

It is a further object of the present invention to provide a technique for the determination of $CO_2$ and $O_2$ in body fluids which does not require the need for measurement of transient responses nor the recording of such transients.

It is a still further object of this invention to provide a method for measuring $CO_2$ and $O_2$ in body fluids such as blood which does not require large sample volumes.

It is still another object of this invention to provide a method for measurement of $CO_2$, $O_2$ and Cl in body fluids without requiring volumetric or manometric measurement.

It is another object of this invention to provide a technique for measurement of $CO_2$ and $O_2$ in body fuids which provides such measurements very quickly.

BRIEF SUMMARY OF THE INVENTION

This invention provides an improved technique for the determination of $CO_2$ and $O_2$ content in samples of body fluid such as whole blood and blood serum. Additionally, modifications are readily made to determine the presence of chlorides in the sample to be tested. Typically, a known amount of sample (blood serum, plasma, or whole blood) is introduced into a vessel. The vessel is then closed and the sample is stirred with a small amount of reagent present so that $CO_2$ or $O_2$ is released from the sample and the gas space in the vessel is equilibrated with the $CO_2$ or $O_2$ from the sample. The release of $CO_2$ or $O_2$ into the gas space is at atmospheric pressure, rather than into a vacuum as is generally practiced in the prior art.

After the gas space has been equilibrated with the released gas, a displacement liquid (such as reagent) is introduced into the vessel, which pushes the equilibrated gas into a detector connected to the gas space of the closed vessel. After the displacement of some of the gas from the gas space into the detector, the detector measures the concentration of a stationary sample of $CO_2$ or $O_2$. This measurement can be displayed conveniently for the operator to view.

After the measurement is made, the mixture of sample and reagent in the closed vessel is then drained from the vessel and excess flushing fluid (such as air in the case of $CO_2$ or He in the case of $O_2$) is passed through the detector and through the vessel in order to flush the apparatus prior to making another measurement. The volume of fluid flushed through the entire apparatus is significantly greater than the volume of the closed vessel, thereby insuring that proper cleansing will occur. The flow of flushing fluid through the apparatus is in a reverse direction to the direction of movement of the released gas to the detector.

The apparatus utilized comprises a vessel which can be closed after introduction of a sample therein and which is adapted to receive a reagent which interacts with the sample to release $CO_2$ to $O_2$. When closed, the vessel is at substantially atmospheric pressure.

The vessel is connected to a detector via a conduit. When a displacement liquid is added by a pump means, the equilibrated released gas in the gas space is pushed via the conduit to the detector where a stationary measurement is made. That is, this apparatus does not rely on the flow of gases through a column in order to provide accurate measurements. As mentioned previously, this removes any of the stringent requirements usually present in blood gas detectors.

Means is provided to remove waste, reagent and sample from the vessel and from the detector after the measurement is made. This waste removal means includes a pump which moves a large volume of flushing fluid (such as air or He) through the detector and through the closed vessel in order to provide proper cleansing.

A controller can be provided for automatically timing the operation of all of the various devices in this apparatus in order to insure fast, reliable measurements. In this regard, it should be noted that this technique for $CO_2$ or $O_2$ measurement in body fluids such as blood, etc. is considerably faster than existing techniques for the performance of such measurements.

If desired, automatic dispensing apparatus can be provided for dispensing the sample to be tested into the vessel in which the reaction to release gas occurs. The dispenser can also operate under control of the timing controller and can, for instance, be associated with a turntable having the samples contained thereon.

It is also possible to modify the vessel somewhat to provide optical equipment for the measurement of chlorides in the sample. A light source of proper wavelength and light guides are provided so that light will be passed through the vessel and then to a detector. This is a conventional colorimetric or spectrophotometric apparatus for determining chloride content.

Thus, this technique for measuring $CO_2$ and $O_2$ in very small samples such as blood serum and whole blood provides a simple, quick and reliable measurement of a stationary sample as opposed to a flowing gas sample. The $CO_2$ or $O_2$ to be measured is released at substantially atmospheric pressure rather than into a vacuum and the released gas is displaced into a detector using a displacement liquid where the liquid volume used to push the gas to the detector is such that the reagent does not get into the detector. The volume of reagent added is a function of the volume of the detector, the tubing connecting the various components in the apparatus, and the vessel. Additionally, the detector and vessel and all connecting lines are flushed in a reverse direction with a flushing fluid in order to insure the accuracy of subsequent analytical measurements. When $CO_2$ is to be measured, the air which is present in the system at atmospheric pressure will not adversely affect the measurement since the thermal conductivity of air, and hence its effect on the detector, is different from that of $CO_2$. Thus, no complicated apparatus is required for separation of gas constituents and no additional reagents have to be added in order to separate $CO_2$ from other gases which may affect the accuracy of the measurements.

These and other objects, features and advantages will be more apparent from the following more particular description of the invention.

DETAILED DESCRIPTION OF THE PREFERRED EMBODIMENTS

Figure 1:
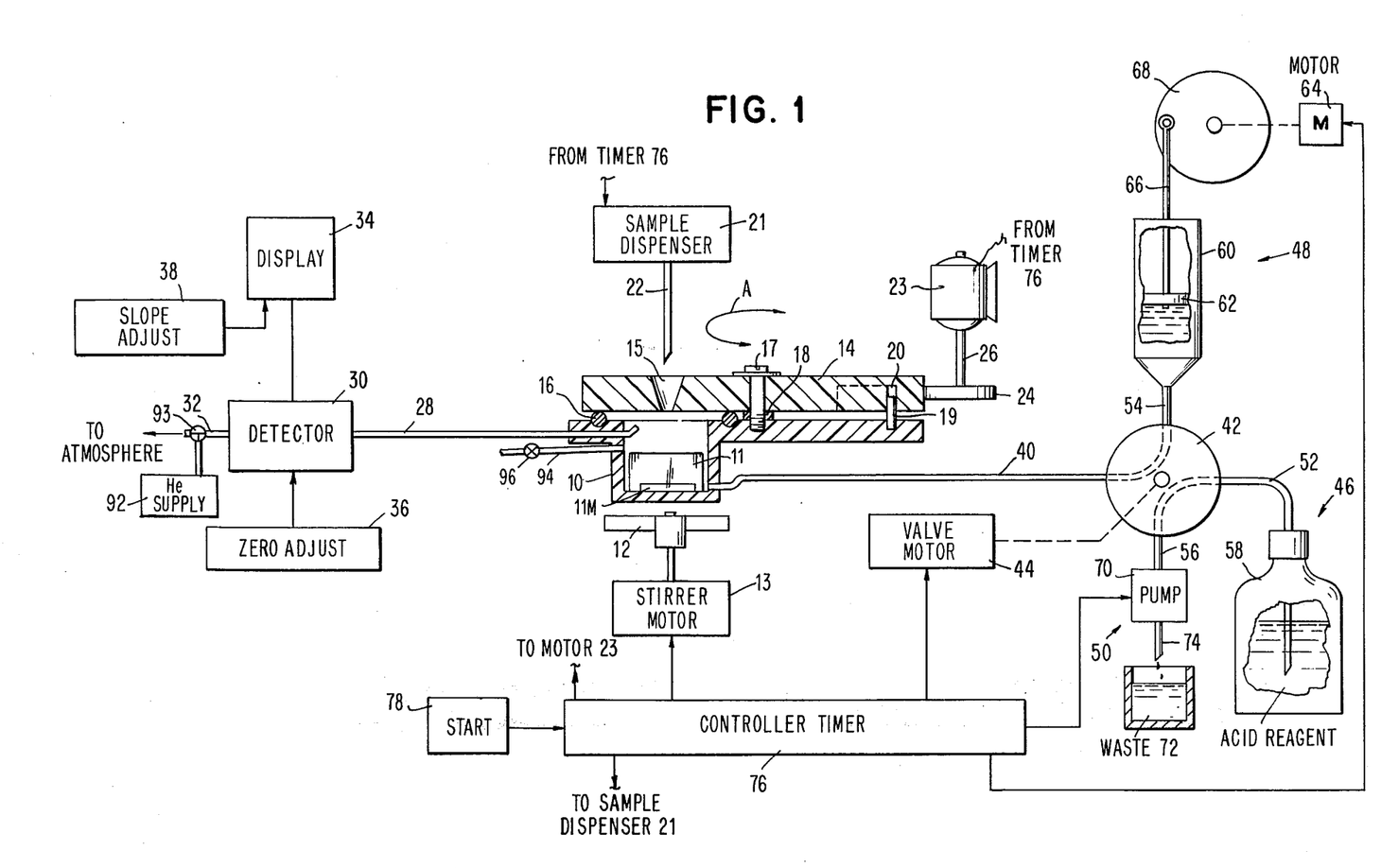
FIG. 1 is a schematic view of an apparatus for practicing the improved $CO_2$ and $O_2$ measurement techniques described herein.

FIG. 1

The apparatus of FIG. 1 will be described generally without particular regard to whether $O_2$ or $CO_2$ is to be determined. After this, operation of the apparatus for detection of $CO_2$ and $O_2$ will be described in more detail.

A vessel 10 is provided which can be closed and in which the sample is placed together with a reagent such as acid, which reacts with the sample to release gas ($CO_2$ or $O_2$) from the sample. As mentioned, the sample is comprised of a body fluid, such as blood serum, whole blood, blood plasma, etc. as typical examples. In the rest of the specification, the sample will be generally indicated as blood or body fluid in order to facilitate the description. Located in vessel 10 is a stirring bar 11 which has a magnetic portion 11M that is driven by magnet 12 which is in turn connected to stirrer motor 13.

Stirrer 11 is used to enhance release of the gas to be detected in the gas space of vessel 10. It does this by increasing the interface area of the sample/reagent solution and the gas space in vessel 10.

A stirrer 11 such as that shown in FIG. 1 can be used to create a thin film of the sample/reagent solution along the walls of vessel 10. For instance, if the stirrer has a length l close to the inner diameter $d$ of vessel 10, a thin film of the solution will be formed along the walls of vessel 10. For $d - l < 1$ mm, a thin film of thickness $< 1$ mm will be formed. For a vessel having a height of 15 mm and volume about 2 ml, the stirrer can be about 12 mm high and about 10 mm wide. By using a stirrer such as this, more than 95% of the gas to be detected will be released in less than 20 seconds, in contrast with previous techniques (such as Natelson, referenced previously) requiring stirring times of about one minute.

Additionally, stirrer 11 can have any number of blades, rather than being two-bladed as shown in FIG. 1. This will further increase the solution/gas space interface area. As can be appreciated, this invention provides a thin film of solution by using a large stirrer and a small volume of sample.

Vessel 10 has associated therewith a moveable cover 14, having an opening 15 therein. Cover 14 rests against O-ring 16 and exerts pressure thereon to close the top opening of vesel 10. Opening 15 can be brought into and out of communication with the top opening of vessel 10 depending on the rotation of cover 14. That is, cover 14 can be rotated in reverse directions in accordance with arrow A in order to provide access to the interior of vessel 10.

Vessel 10 and cover 14 are generally comprised of materials which are chemically inert and which will not influence the reaction of the sample and the reagent. Suitable materials are plastics and glasses. In FIG. 1, cover 14 is held in contact with O-ring 16 by an alignment and fastening means 17, which is conveniently a screw which is surrounded by a bushing 18. A pin 19, located in the top surface of vessel 10 travels in a guide 20 in cover 14 in order to limit the motion of cover 14 which is used to bring opening 15 into and out of communication with the top opening of vessel 10.

During operation, the filling hole 15 is over vessel 10 so that a sample can be placed in vessel 10. The sample can be placed in vessel 10 by an operator using a suitable instrument such as a pipette, or placement can be done automatically. An automatic operation will typically use a sample dispenser 21 which may receive samples from a turntable (not shown). The sample is then discharged through tubing 22 in order to enter vessel 10. All of this operation can be done automatically under control of separate circuitry, as will be described later.

Movement of the cover plate 14 to bring filling hole 15 into and out of contact with the top of vessel 10 can be done by a driving means comprising a motor 23 and a drive wheel 24 which is connected to the motor via drive shaft 26. The operation can also be done automatically and synchronized with the operation of the sample dispenser 21, through the use of appropriate control circuitry.

The volume of vessel 10 is chosen in accordance with the typical amount of sample to be tested. For example, vessel 10 has a volume which is typically of the order of 1 ml. The volume of vessel 10 has be larger than the combined volume of line 28 and detector 30 so that line 28 and detector 30 can be flushed when the equilibrated gas is transferred. Also, the volume of additional reagent injected to transfer the equilibrated gas is less than the volume of line 28 plus the volume of vessel 10, to prevent reagent from entering detector 30. Thus, the volume of the displacement reagent used to transfer gas to the detector is less than the volume of vessel 10 minus the volume of stirrer 11.

Thin tubing 28 connects vessel 10 with a detector 30. Detector 30 may a thermal conductivity detector containing thermistors or hot wire filaments as is generally well known. Thermal conductivity detectors (also called katharometers) usually measure the heat loss through a gas from the prime heat source (filament or thermistor) into a cell block or heat sink. The detector elements or heat sources are organized in a Wheatstone Bridge permitting the imbalance resulting from the change in a sample gas to be read on a meter, etc. The detector elements may, for example, be thermistors or hot wires made of tungsten, tungsten alloys or other suitable materials. For a review of such detectors, reference is made to an article by A. E. Lawson et al., entitled "Thermal Conductivity Detectors in Gas Chromatography", which appeared in Gas Chromatography, Vol. 4, page 273 (1966). Depending upon the thermal conductivity of the gas in contact with the wire filament, the detector will provide an indication of the concentration of the gas in contact with the wire filament. These detectors are manufactured and sold by a number of companies, such as Beckman Instruments, Fullerton, Calif., Fisher Scientific, Pittsburgh, Pa., among others.

Detector 30 is provided with an output tubing vent 32, which is used for the flushing operation to be described later.

When vessel 10 has a volume of about 1 ml. the thin tubing will typically have a volume of only about 0.1 ml or less. For these volume dimensions, the internal volume of detector 30 should preferably not be larger than about 0.1 – 0.2 ml.

Detector 30 is connected in a conventional bridge circuit to display 34 which indicates the amount of $CO_2$ being detected. The bridge circuit can also include a zero adjust circuit 36 and a slope adjust circuit 38 which is used for calibration purposes. Thus, a detection means for indicating the concentration of $CO_2$ in the sample is generally comprised of detector 30, display 34, zero adjust 36, and slope adjust 38.

Vessel 10 is also controllably connected to a means for putting a reagent into the vessel, a means for adding displacement fluid to the vessel to expel released gas into tubing 28, and a means for flushing the detector and vessel 10 after a sample analysis is made. These various means are generally connected to vessel 10 via tubing 40, through the action of a rotary valve 42. Valve 42 is driven by valve motor 44 which can be automatically controlled by appropriate timer circuitry, as will be described. The means for putting reagent into vessel 10 initially is generally designated 46, the means for adding displacement fluid to expel the released gas from vessel 10 is generally indicated by numeral 48, while the means for flushing the vessel 10 and detector 30 after an analysis is generally indicated by numeral 50.

Various lines are used to controllably connect these various means 46, 48 and 50 to tubing 40 which communicates with vessel 10. Rotary valve 42 can make and break connections to line 52 which goes to means 46, to line 54 which goes to means 48, and to line 56 which goes to means 50.

Reagent means 46 generally comprises a container 58 for storing the reagent used to react with the sample. For measurement of $CO_2$, this reagent is generally an acid such as a 1M aqueous solution of lactic acid.

The reagent adding means 48 is used to provide a small amount of displacement fluid (such as reagent) into vessel 10 in order to push released gas to the detector 30. Means 48 is typically comprised of a cylinder 60 having a moveable piston 62 therein. The reagent used in the detection is also preferably present in cylinder 60. Piston 62 is driven by a motor 64 which is connected to shaft 66 via ecentric 68. Motor 64 can also be under control of an appropriate timing circuit to automate the actuation of means 48 at the proper time. While transfer of the gas mixture in the vessel gas space is preferably done by using a displacement fluid other methods, such as pumping, can be used to accomplish the transfer.

Flushing means 50 is generally comprised of a pump 70 which removes reagent and sample from vessel 10 and also removes released gas from detector 30 and vessel 10 after a measurement has been made. The flushed material is released into waste container 72 via tubing 74. The operation of pump 70 can also be controllably activated by appropriate control circuitry. Additionally, means 50 moves a flushing fluid through the detector 30, tubing 28, and vessel 10, to cleanse these parts prior to each new measurement.

A controller timer 76 is actuated by start circuit 78 and is used to control the operation of stirrer motor 13, sample dispenser 21, drive motor 23, valve motor 44, motor 64, pump 70 and all valves. Timer 76 provides start signals to each of these components at the proper time to provide totally automatic operation in order to determine $CO_2$ or $O_2$ content from a sample of body fluid placed in vessel 10. This automatic operation includes a flushing step which cleanses detector 30 and vessel 10 after each individual sample measurement is made, and which actuates the beginning of another sample measurement. Consequently, measurements numbering approximately 60 (or more) per hour can be made by this apparatus in contrast with prior art measurement speeds typically less than 10 measurements per hour.

$CO_2$ Analysis Operation

To inject the sample of body fluid to be tested into vessel 10, cover 14 is moved so that opening 15 is over the top opening of the vessel 10. This sample can have very small volume, as for instance, 0.01 ml. Thus, pediatric samples can be easily analyzed. The sample to be analyzed is injected into vessel 10 by an operator or by automatic dispensing equipment 21. Vessel 10 is then closed by turning cover 14 to move opening 15 away from the top opening of the vessel. If the movement of cover 14 is under control of timer 76, a signal will be provided to motor 23 and to sample dispenser 21 to initiate this operation. Controller timer 76 then provides a signal to valve motor 44 which causes the rotary valve 42 to connect lines 40 and 52 so that acid reagent will be introduced into vessel 10. In most measurements, the small amount of strong acid remaining on the walls of vessel 10 from the previous measurement cycle will be sufficient for reaction with the blood sample in order to release $CO_2$. Thus, initial amounts of reagent may or may not be required from source 58.

The timer 76 starts stirrer motor 13 which mixes the sample and reagent in vessel 10, by means of stirrer bar 11. The sample and reagent react to release $CO_2$ into the gas space in vessel 10 which is thus equilibrated. After about 20–30 seconds, timer 76 actuates motor 44 which rotates the rotary valve 42 in order to cause lines 40 and 54 to communicate with one another. Motor 64 is then actuated to push acid reagent (displacement fluid) from cylinder 60 into vessel 10, through the action of piston 62. The volume of reagent pushed into vessel 10 by the movement of piston 62 is chosen such that vessel 10 is not completely filled in order to avoid contaminating the gas detector 30 with reagent. As an example, for a vessel volume of 1 ml a typical volume of reagent to be injected by piston 62 is 0.7 – 0.8 ml (if no reagent were initially put into vessel 10 for release of $CO_2$).

The injection of reagent into vessel 10 displaces the equilibrated gas volume from vessel 10 into detector 30. It is preferable that the flow of gas is essentially stopped before the measurement is made. Since the displacement liquid in cylinder 60 is only used to push equilibrated $CO_2$ into detector 30, it need not be the reagent used for release of $CO_2$. For instance, any substance which would not absorb $CO_2$ and which would not overpower the reagent in vessel 10 to adversely affect the next measurement is suitable. Aqueous solutions containing salt are examples. The signal produced by detector 30 is displayed by display 34 where it can be easily read by the operator. Controller timer 76 may then be stopped at this time to allow the operator time to read and record the displayed signal and to permit him to set the slope adjustment circuit 38 when running a calibration sample. After these operations, timer 76 may be restarted. The timer actuates motor 44 so that lines 40 and 56 are now communicating with one another. Pump 70 is also actuated by timer 76 causing vessel 10 to be drained and also drawing an excess of fresh air into vessel 10. It is important that not only the liquid is drained from vessel 10, but also that all of vessel 10 is filled with fresh air (through detector 30) so that the $CO_2$ equilibrated air is removed from the system. The amount of excess air drawn through the detector and vessel 10 is sufficient to provide good drainage of these units. For instance, a volume of at least approximately five times the volume of vessel 10 is suitable.

Valve motor 44 then connects lines 52 and 54 in order to fill cylinder 60 with reagent by means of motor 64. The valve motor 44 then moves rotary valve 42 in order to connect lines 54 and 40. This pushes a small amount of reagent into the lines so that line 40 is filled and possibly a small amount of reagent (for instance 0.05 ml) gets into vessel 10.

As noted, it has been found that the apparatus also works well without injection of reagent into vessel 10 via piston 62, since the small amount of strong acid remaining on the vessel walls from the previous cycle is generally sufficient for reaction with the next blood sample.

The apparatus is now ready for the next sample. Before injecting the next sample or before the timer 76 actuates sample dispenser 21, the operator may check the display 34 which should read zero and may also set zero adjust circuit 36 to obtain a zero reading.

In the practice of this invention, it has been found that equilibrium between the acidified sample and the gas space in vessel 10 is more efficient when detergent is added to the acid reagent. For example, a solution of 1M lactic acid containing 5% by volume of polyoxyethylene (20) sorbitan monooleate, a commercially available surfactant, can be used.

Figure 2:
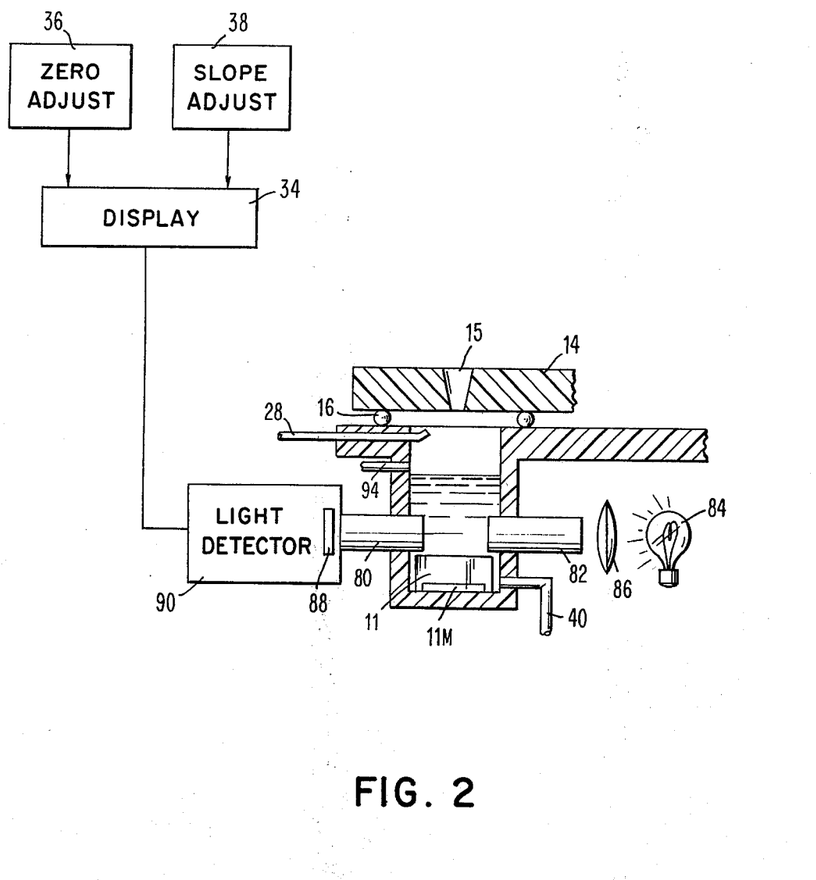
FIG. 2 is a schematic diagram of a portion of the apparatus of FIG. 1, which is modified to provide a measurement of Cl in the test sample.

Cl Analysis — FIG. 2

Gas analysis as taught herein may be combined with that for Cl by modifying the apparatus of FIG. 1. The determination of Cl is carried out simultaneously with the gas analysis by the method of Zall, as described in Analytical Chemistry 28, page 1665, (1956). In the method of Zall, blood serum is mixed with an acid reagent containing mercuric thiocyanate and ferric perchlorate. This reagent yields a red color in the present of Cl which can in turn be measured at a wavelength of, for example, 480 nm to give the Cl concentration. Since the reagent is strongly acidic, it may be used instead of lactic acid to release $CO_2$ from the blood serum into the gas space of vessel 10.

FIG. 2 shows a modified version of the apparatus of FIG. 1 which can be used for the combined determination of $CO_2$ or $O_2$ and $Cl^-$. Only a portion of the total apparatus of FIG. 1 is shown; consequently, many portions of the apparatus of FIG. 1 which would be the same as that in FIG. 2 (such as the means 46 and 48, etc.) are not shown for ease of illustration.

In FIG. 2, vessel 10 has a cover 14 having an opening therein which can be moved into and out of communication with the opening in the top of vessel 10. As previously noted, cover 14 bears against O-ring 16 in order to provide proper closure of the vessel when such is desired. Also, line 28 which brings equilibrated gas to the detector (not shown) is partially indicated. The tubing line 40 is also partially shown in this drawing, while stirrer 11 is indicated. Display 34, zero adjust circuit 36, and slope adjust circuit 38 are also shown in this drawing. These components are used in conjunction with a light detector used for Cl determination, and can also be used in combination with the gas detector 30 described previously.

Vessel 10 is modified and includes light guides 80 and 82 in its walls. A light source 84, a collimating lens 86, a filter 88, and a light detector 90 are also provided. Light from source 84 is collimated by lens 86 and then enters vessel 10 through light guide 82. After passing through the solution to be measured, the light leaves vessel 10 via light guide 80 and is incident on filter 88 and then light detector 90. Detector 90 accepts only light which has been passed by filter 88 (which can be transmitting, for instance, at 480 nm).

This source-detector apparatus is representative of any colorimetric or spectrophotometric apparatus, which may be a single beam, double beam, single wavelength or double wavelength apparatus, all of which are well known in the art for analytical measurement. The output of this analytical instrumentation is then displayed directly in concentration units of chloride.

Operation of FIG. 2 Apparatus

The operation of the modified apparatus of FIG. 2 is closely identical to that described previously. The Zall reagent is used instead of the simple lactic acid. After the gas volume is displaced from vessel 10 into detector 30 by the addition of reagent, both measurements are now carried out. The gas concentration is read in the gas detector 30 and the $Cl^-$ concentration is read from the color intensity of the reagent, the reagent filling the optical gap between guides 80 and 82.

Oxygen ($O_2$) Determination

The apparatus shown in FIG. 1 may also be used for the determination of $O_2$ in body fluids such as blood.

The determination of $O_2$ in blood is a frequently performed test, being used for example in anesthesiology. At present, equipment for performing this measurement uses the Van Slyke and Natelson Gasometric methods, or gas chromatographic methods, mentioned previously.

In order to determine $O_2$ content using the apparatus of FIG. 1, some modifications are made. These are:

1. The reagent is chosen to release oxygen from blood. Such reagents are well known in the literature and can contain per liter, the following components: 8 grams saponin, 32 grams potassium ferricyanide, and 1 ml of antifoam (General Electric Company Antifoam 60). This reagent solution may also contain an anticoagulant such as heparin to prevent clotting of the blood. It is generally preferable that the pH of such a reagent be above pH 8 so that $CO_2$ is not released, but rather is bound by the reagent in the form of bicarbonate or otherwise.

2. The vessel 10, line 28, and detector 30 are not filled with air, but are filled with another gas having a different thermal conductivity than the species to be measured. Such a gas could be, for example, He. The thermal conductivities of He and $O_2$ in units of Cal/cm$^2$ sec./°C cm. are He : $34.3 \times 10^5$ and $O_2$ : $5.8 \times 10^{-5}$. In order to fill the apparatus with helium, a helium supply 92 (FIG. 1), essentially at atmospheric pressure, is connected to outlet line 32 of detector 30 via three-way valve 93. When the apparatus is flushed by pump 70, helium is drawn through detector 30, line 28, and vessel 10 before each new analysis begins. After the apparatus is filled with He, and pump 70 has stopped, the three-way valve 93 is turned automatically so that the detector 30 and vessel 10 are at atmospheric pressure.

3. The apparatus is provided with a rubber septum through which a body fluid sample to be measured may be injected with a needle and syringe (generally included in sample dispenser 21) so that no air will enter vessel 10.

In operation, the operator injects a known amount of sample, for instance 0.100 ml, through the rubber septum into vessel 10, which contains a certain volume of the oxygen releasing reagent. Stirrer 11 is rotated to assist the release of oxygen from the sample into the gas space of vessel 10. After this, additional reagent (displacement liquid) is injected into vessel 10 via line 40 in order to displace some of the oxygen-helium gas mixture into detector 30. The injection of displacemennt fluid is now stopped and the detector measures the oxygen content of a stationary gas sample in the detector. The result can be visually displayed using display 34.

The operator then initiates the flushing cycle which drains the reagent and the old body fluid sample from vessel 10 through lines 40 and 56. The valve then connects He supply 92 to line 32. This flushes detector 30, line 28, and vessel 10 with fresh helium from source 92.

A new amount of reagent, for example, 0.1 or 0.2 ml, is then introduced from cylinder 60 into vessel 10. Since this reagent may contain oxygen, an additional step may be required to remove oxygen from the reagent. This additional step requires that stirrer 11 be rotated to release the dissolved oxygen from the reagent into the gas space of vessel 10. Additional helium is then passed through vessel 10 from supply 92. This helium passes through vessel 10 and exits through line 94 which can be automatically closed by a valve 96. The apparatus is now ready for the next oxygen analysis, since the gas space in vessel 10 contains only helium and since all oxygen has been removed from the reagent.

what has been described is a unique method and apparatus for $CO_2$ and $O_2$ measurement in body fluids such as whole blood and blood serum. This technique is characterized by the release of $CO_2$ and $O_2$ into a gas space which is at atmospheric pressure rather than being at a vacuum. The method is extremely simple and can be modified by those having skill in the art. When the sample to be measured is changed, for instance when going from blood serum to whole blood, the reagent used is chosen in accordance with the sample, which reagents are well known. Also, while thermal conductivity detectors are preferable because of their high accuracy, speed, and simplicity, other gas detectors known in the art may be used for the practice of this technique.

The method is characterized by measuring a stationary sample rather than a flowing gas sample, and by the displacement of the gas to be detected through the use of a liquid, such as the reagent. The reagent volume is less than the vessel volume in this operation. Additionally, the method comprises the steps of draining the detector, the vessel, and the tubing lines in a reverse direction with an excess of fluid (such as air, He, etc.). Thus, this technique provides a simple and reliable technique for the analysis of $CO_2$ and $O_2$ and can be used to provide increased speed of measurement while maintaining high accuracy. Also, the apparatus can be modified to enable one to make chloride measurements simultaneously with the gas measurements. In all cases, the amount of sample meeded is very small, and the composition of the stationary sample measured in the detector is essentially the same as that in the vessel gas space after the gas to be detected is released from the body fluid sample.

Thus, the invention broadly encompasses the alteration of a gas mixture in a gas space by a reaction between a sample of body fluid and a reagent. The altered gas mixture is then transferred to a detector, preferably by using a displacement liquid. The altered gas mixture is then measured, and the vessel is then drained. Flushing of the detector and the vessel then occurs by a large reverse flow of a flushing fluid.

Thus, it will be appreciated that the method and apparatus described here may be used to determine species other than $O_2$ and $CO_2$ in body fluids. Whenever gases are released or are bound by a reaction of a species with a reagent, the present apparatus can be used for detection. For example, uric acid in the presence of the enzyme uricase reacts with oxygen, as is well known. The consumption of oxygen may be used for uric acid detection. The reagent used can be a solution of uricase while the gas used for flushing would be a He-$O_2$ mixture having, for instance, 20% $O_2$, 80% He.

In operation, a small amount (say 0.1 ml) of the enzyme solution is pumped into the vessel reaction chamber, and the system is flushed with the He-$O_2$ mixture. The mixture is stirred so that the gas dissolved in the enzyme solution equilibrates with the He-$O_2$ mixture. The system is then flushed again with fresh He-$O_2$. The blood to be tested for uric acid is then introduced through a septum. The reaction between uric acid and oxygen is now proceeding in the vessel. The solution is stirred to facilitate the oxygen dissolution in the solution. After a preset time, the reacted He-$O_2$ mixture is transferred into the detector where the loss of oxygen measured is directly proportional to the uric acid concentration.

What is claimed is:

1. A method for measuring $CO_2$ in a sample of body fluid, comprising the steps of:

reacting said sample and a reagent in a vessel to release $CO_2$ into a gas space filled substantially with air at essentially atmospheric pressure to produce a mixture of said released $CO_2$ and air, said gas space having a volume greater than the volume of sample in said vessel, transferring at least a portion of said mixture in said gas space to a detector by adding a displacing liquid to said vessel, and measuring the concentration of said transferred gas mixture in said detector.

2. The method of claim 1, where said displacing liquid is comprised of said reagent.

3. The method of claim 1, where the volume of displacing liquid added to said vessel is less than the volume of said vessel.

4. The method of claim 1 where said detector measures a stationary sample of said transferred gas mixture.

5. The method of claim 4, where said detector measures the thermal conductivity of said transferred gas mixture.

6. The method of claim 1, including the further steps of draining said sample and reagent from said vessel after said measuring step, and then flushing said detector and said vessel with air which moves in a direction reverse to the direction of transfer of said gas mixture.

7. The method of claim 1, including the further step of measuring $Cl^-$ in said body fluid by passing an optical beam through said sample and reagent in said vessel, and measuring the intensity of said beam at a given wavelength after passage of said beam through said sample and reagent.

8. The method of claim 1, where said body fluid is comprised of one of the group consisting essentially of whole blood, blood serum, and blood plasma.

9. A method for measuring $CO_2$ in a sample of body fluid, comprising the steps of:

reacting said sample and a reagent in a vessel to release $CO_2$ from said sample into a gas space filled substantially with air to produce a mixture of said released $CO_2$ and air, said gas space having a volume greater than the volume of sample in said vessel, transferring at least a portion of said gas mixture in said gas space to a detector, measuring a stationary sample of said transferred gas mixture in a thermal conductivity detector, 10. The method of claim 9, including the further steps of draining said sample and reagent from said vessel after said measuring step and then flushing said detector and said vessel with air which moves in a direction reverse to the direction of transfer of said gas mixture from said gas space to said detector.

11. The method of claim 9, where the release of $CO_2$ from said sample is enhanced by forming a thin film of sample plus reagent along the walls of said vessel, said thin film being less than about 1 mm in thickness.

12. The method of claim 9, where said $CO_2$ is released into said gas space at substantially atmospheric pressure.

13. The method of claim 9, where said body fluid is selected from the group consisting essentially of whole blood, blood plasma, and blood serum.

14. A method for measuring $CO_2$ in a sample of body fluid, comprising the steps of:

reacting said sample and a reagent in a vessel to release $CO_2$ into a gas space filled substantially with air at essentially atmospheric pressure to produce a mixture of said released $CO_2$ and air, transferring at least a portion of said gas mixture in said gas space to a detector, measuring the concentration of said transferred gas mixture in said detector, draining said sample and said reagent from said vessel, and flushing said detector and said vessel after said measurement with air which moves through said detector in a direction reverse to the direction of transfer of said gas mixture from said gas space to said detector.

15. The method of claim 14, including the step of creating a thin layer of said sample plus reagent along the walls of said vessel to enhance release of said $CO_2$ into said gas space, said layer being less than about 1 mm in thickness.

16. The method of claim 14, where said transferring occurs by adding a displacing liquid to said vessel, thereby expelling at least a portion of said gas mixture in said gas space to said detector.

17. A method for determining $CO_2$ in a sample of body fluid, comprising the steps of:

reacting said sample and a reagent in a vessel to release $CO_2$ from said sample into a gas space having air therein to produce a gas mixture of said released $CO_2$ and air, transferring at least a portion of said gas mixture in said gas space to a thermal conductivity detector by adding a displacing fluid to said vessel to force said gas mixture out of said gas space to said detector, measuring the concentration of a stationary sample of said transferred gas mixture in said detector, draining said sample and said reagent from said vessel, and flushing said detector and said vessel after said measuring step with air which moves in a direction reverse to the direction of movement of said gas mixture from said gas space to said detector.

18. The method of claim 17, including the further step of enhancing the release of $CO_2$ from said sample into said gas space by forming a thin film of said sample plus reagent in said vessel, said thin film having a thickness less than about 1 mm.

19. The method of claim 17, where said body fluid is selected from the group consisting essentially of whole blood, blood serum, and blood plasma.

20. The method of claim 12 including the further step of determining $Cl^-$ in said sample by passing a light beam through said sample plus reagent in said vessel, and measuring the intensity of said beam at a given wavelength after passage of said beam through said sample and reagent.

21. The method of claim 17, where said vessel is connected to said detector by a tubing, the volume of said vessel being greater than the combined volume of said detector and said tubing.

22. The method of claim 17, where said vessel has a stirrer therein for enhancing said sample-reagent reaction, the volume of said displacing liquid added to said vessel being less then the volume of said vessel minus the volume of said stirrer.

23. A method for measuring $CO_2$ in a sample of body fluid, comprising the steps of:

reacting said sample and a reagent in a vessel to release $CO_2$ into a gas space filled substantially with air to produce a mixture of said releasesd $CO_2$ and air, transferring at least a portion of said mixture in said gas space to a detector, thermally detecting $CO_2$ in a stationary sample of $CO_2$ and air in said detector.

24. A method for detection of a species in a sample of fluid, comprising the steps of:

placing said sample and a reagent in a vessel having a gas space with a given gas mixture therein to react said sample and said reagent to alter the composition of said given gas mixture, transferring at least a portion of said altered gas mixture to a detector by adding a displacing liquid to said vessel, measuring a stationary sample of said altered gas mixture in said detector, draining said sample and reagent from said vessel, and flushing said detector and said vessel with a flushing fluid which moves in a direction reverse to the direction of transfer of said altered gas mixture from said gas space to said detector.

25. A method for measuring $O_2$ in a sample of body fluid, comprising the steps of:

reacting said sample and a reagent in a vessel to bind $CO_2$ in said sample and to release $O_2$ into a gas space filled substantially with a first gas at essentially atmospsheric pressure to produce a mixture of said released $O_2$ and said first gas, said gas space having a volume greater than the volume of sample in said vessel, transferring at least a portion of said mixture in said gas space to a detector by adding a displacing liquid to said vessel, and measuring the concentration of said transferred gas mixture in said detector.

26. The method of claim 24, where said displacing liquid is comprised of said reagent.

27. The method of claim 25 where said detector measures a stationary sample of said transferred gas mixture.

28. The method of claim 27, where said detector measures the thermal conductivity of said transferred gas mixture, said first gas having a different thermal conductivity than $O_2$.

29. The method of claim 25, including the further steps of draining said sample and reagent from said vessel after said measuring step, and then flushing said detector and said vessel with said gas which moves in a direction reverse to the direction of transfer of said mixture.

30. A method for measuring $O_2$ in a sample of body fluid, comprising the steps of:

reacting said sample and a reagent in a vessel to bind $CO_2$ in said sample and to release $O_2$ from said sample into a gas space filled substantially with a first gas having a different thermal conductivity than $O_2$ to produce a mixture of said released $O_2$ and said first gas, said gas space having a volume greater than the volume of sample in said vessel, transferring at least a portion of said gas mixture in said gas space to a detector, measuring a stationary sample of said transferred gas mixture in a thermal conductivity detector.

31. The method of claim 30, including the further steps of draining said sample and reagent from said vessel after said measuring step and then flushing said detector and said vessel with said first gas which moves in a direction reverse to the direction of transfer of said gas mixture from said gas space to said detector.

32. The method of claim 30, where the release of $O_2$ from said sample is enhanced by forming a thin film of sample plus reagent along the walls of said vessel, said thin film being less than about 1 mm in thickness.

33. The method of claim 30, where said $O_2$ is released into said gas space at substantially atmospheric pressure.

34. A method for measuring $O_2$ in a sample of body fluid, comprising the steps of:

reacting said sample and a reagent in a vessel to bind $CO_2$ in said sample and to release $O_2$ into a gas space filled substantially with a first gas at essentially atmospheric pressure to produce a mixture of said released $CO_2$ and said first gas, transferring at least a portion of said gas mixture in said gas space to a detector, measuring the concentration of said transferred gas mixture in said detector, draining said sample and reagent from said vessel, and flushing said detector and said vessel with said first gas which moves through said detector in a direction reverse to the direction of transfer of said gas mixture from said gas space to said detector.

35. The method of claim 34, including the step of creating a thin layer of said sample plus reagent along the walls of said vessel to enhance release of said $O_2$ into said gas space, said layer being less than about 1 mm in thickness.

36. The method of claim 34, where said transferring occurs by adding a displacing liquid to said vessel, thereby expelling at least a portion of said gas mixture in said gas space to said detector.

37. A method for determining $O_2$ in a sample of body fluid, comprising the steps of:

reacting said sample and a reagent in a vessel to bind $CO_2$ in said sample and to release $O_2$ from said sample into a gas space having a first gas having a different thermal conductivity than $O_2$ therein to produce a gas mixture of said released $O_2$ and said first gas, transferring at least a portion of said gas mixture in said gas space to a thermal conductivity detector by adding a displacing fluid to said vessel to force said gas mixture out of said gas space to said detector, measuring the concentration of a stationary sample of said transferred gas mixture in said detector, draining said sample and said reagent from said vessel, and flushing said detector and said vessel with said first gas which moves in a direction reverse to the direction of movement of said gas mixture from said gas space to said detector.

38. The method of claim 37, including the further step of enhancing the release of $O_2$ from said sample into said gas space by forming a thin film of said sample plus reagent in said vessel, said thin film having a thickness less than about 1 mm.

39. The method of claim 37, where said body fluid is selected from the group consisting essentially of whole blood, blood serum, and blood plasma.

40. The method of claim 24, including the further step of determining $Cl^-$ in said sample by passing a light beam through said sample plus reagent in said vessel, and measuring the intensity of said beam at a given wavelength after passage of said beam through said sample and reagent.

41. The method of claim 37, where said detector is connected to said vessel by a tubing, the volume of said vessel being greater than the combined volume of said detector and said tubing.

42. The method of claim 37, where said vessel has a stirrer therein for enhancing the sample-reagent reaction, the volume of displacing liquid added to said vessel being less than the volume of said vessel minus the volume of said stirrer.

43. A method for measuring $O_2$ in a sample of body fluid, comprising the steps of:
reacting said sample and a reagent in a vessel to bind $CO_2$ in said sample and to release $O_2$ into a gas space filled substantially with a first gas having a different thermal conductivity than $O_2$ to produce a mixture of said released $O_2$ and said first gas,
transferring at least a portion of said mixture in said gas space to a detector,
thermally detecting $O_2$ in a stationary sample of $O_2$ and said first gas in said detector.

44. A method for measuring $CO_2$ in a sample of body fluid, comprising the steps of:
reacting said sample and a reagent in a vessel to release $CO_2$ from said sample into a gas space having a given gas therein to produce a mixture of said released $CO_2$ and said given gas,
transferring at least a portion of said gas mixture in said gas space to a thermal conductivity detector, and
measuring a stationary sample of said transferred gas mixture in said detector.

45. The method of claim 44, including the further steps of:
draining said sample and said reagent from said vessel, and
flushing said detector and said vessel after said measurement.

46. A method for measuring $O_2$ in a sample by body fluid, comprising the steps of:
reacting said sample and a reagent in a vessel to bind $CO_2$ in said sample and to release $O_2$ from said sample into a gas space filled substantially with a first gas having a different thermal conductivity than $O_2$ to produce a mixture of said released $O_2$ and said first gas,
transferring at least a portion of said mixture in said gas space to a detector,
thermally detecting $O_2$ in a stationary sample of $O_2$ and said first gas in said detector,
draining said sample and said reagent from said vessel, and
flushing said detector and said vessel with said first gas.

47. A method for detection of a species in a sample of fluid, comprising the steps of:
placing said sample and a reagent in a vessel having a gas space with a given gas mixture therein to react said sample and said reagent to alter the composition of said given gas mixture,
transferring at least a portion of said altered gas mixture to a detector by adding a displacing liquid to said vessel,
measuring a stationary sample of said altered gas mixture in said detector,
draining said sample and reagent from said vessel, and
flushing said detector and said vessel with a flushing fluid.

* * * * *